(12) United States Patent
Roe

(10) Patent No.: US 7,211,052 B2
(45) Date of Patent: May 1, 2007

(54) FLEXIBLE TEST STRIP LANCET DEVICE

(75) Inventor: Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 398 days.

(21) Appl. No.: 10/737,026

(22) Filed: Dec. 16, 2003

(65) Prior Publication Data

US 2004/0127929 A1 Jul. 1, 2004

Related U.S. Application Data

(60) Provisional application No. 60/437,002, filed on Dec. 30, 2002.

(51) Int. Cl.
*A61B 5/00* (2006.01)
(52) U.S. Cl. .................. 600/584; 600/583; 600/573; 606/181; 606/182
(58) Field of Classification Search ............ 600/583, 600/584, 573, 576; 606/181, 182
See application file for complete search history.

(56) References Cited

U.S. PATENT DOCUMENTS

| 3,626,929 A | 12/1971 | Sanz et al. |
| 3,802,842 A | 4/1974 | Lange et al. |
| 4,061,468 A | 12/1977 | Lange et al. |
| 4,360,016 A | 11/1982 | Sarrine |
| 4,490,465 A | 12/1984 | Limbach et al. |
| 4,627,445 A | 12/1986 | Garcia et al. |
| 4,648,408 A | 3/1987 | Hutcheson et al. |
| 4,653,511 A | 3/1987 | Goch |
| 4,873,993 A | 10/1989 | Meserol et al. |
| 4,883,068 A | 11/1989 | Dechow |
| 4,920,977 A | 5/1990 | Haynes |
| 4,924,879 A | 5/1990 | O'Brien |
| RE35,803 E | 5/1998 | Lange et al. |
| 5,776,719 A | 7/1998 | Douglas et al. |
| 5,824,491 A | 10/1998 | Priest et al. |
| 5,857,983 A | 1/1999 | Douglas et al. |
| 5,868,772 A | 2/1999 | LeVaughn et al. |
| 5,879,311 A | 3/1999 | Duchon et al. |
| 5,951,492 A | 9/1999 | Douglas et al. |
| 5,951,493 A | 9/1999 | Douglas et al. |
| 5,962,215 A | 10/1999 | Douglas et al. |
| 5,964,718 A | 10/1999 | Duchon et al. |
| 6,048,352 A | 4/2000 | Douglas et al. |

(Continued)

FOREIGN PATENT DOCUMENTS

EP 0 164 148 12/1985

(Continued)

*Primary Examiner*—Max Hindenburg
*Assistant Examiner*—H. Q. Nguyen
(74) *Attorney, Agent, or Firm*—Woodard, Emhardt, Moriarty, McNett & Henry LLP

(57) ABSTRACT

A bodily fluid sampling device includes a flexible test strip, a lancet, and a deflection mechanism. The test strip is biased to be positioned over the incision site formed by the lancet. The deflection mechanism positions the test strip away from the incision site during lancing so as to allow the lancet to have clear access to the incision site. Due to the flexible nature of the test strip, after lancing the incision, the test strip returns to the original position so as to collect fluid from the incision.

16 Claims, 4 Drawing Sheets

U.S. PATENT DOCUMENTS

| | | |
|---|---|---|
| 6,071,250 A | 6/2000 | Douglas et al. |
| 6,071,294 A | 6/2000 | Simons et al. |
| 6,086,545 A | 7/2000 | Roe et al. |
| 6,099,484 A | 8/2000 | Douglas et al. |
| 6,183,489 B1 | 2/2001 | Douglas et al. |
| 6,319,210 B1 | 11/2001 | Douglas et al. |
| 6,332,871 B1 | 12/2001 | Douglas et al. |
| 6,849,052 B2 * | 2/2005 | Uchigaki et al. ............ 600/584 |
| 2002/0169393 A1 | 11/2002 | Cunningham et al. |
| 2002/0188224 A1 * | 12/2002 | Roe et al. .................... 600/584 |
| 2004/0215224 A1 * | 10/2004 | Sakata et al. ................ 606/181 |
| 2005/0261716 A1 * | 11/2005 | Sakata et al. ................ 606/181 |
| 2005/0277850 A1 * | 12/2005 | Mace et al. .................. 600/584 |
| 2005/0288698 A1 * | 12/2005 | Matsumoto .................. 606/181 |

FOREIGN PATENT DOCUMENTS

| | | |
|---|---|---|
| EP | 0 894 471 | 2/1999 |
| EP | 1 238 632 A1 | 9/2002 |
| EP | 1 402 812 A1 | 3/2004 |
| JP | 2000217804 | 8/2000 |
| WO | WO 93/09710 | 5/1993 |
| WO | WO 97/08986 A1 | 3/1997 |
| WO | WO 98/15810 | 4/1998 |
| WO | WO 02/056751 A2 | 7/2002 |

* cited by examiner

FLEXIBLE TEST STRIP LANCET DEVICE

REFERENCE TO RELATED APPLICATIONS

This application claims the benefit of U.S. Provisional Application No. 60/437,002, filed Dec. 30, 2002, which is hereby incorporated by reference in its entirety.

BACKGROUND

The present invention generally relates to bodily fluid sampling devices and more specifically, but not exclusively, concerns an integrated body fluid sampling device that is adapted to position a test strip directly over the incision site.

General Fluid Testing

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of bodily fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

Acquiring—Incising

The other common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

Various methods and systems for incising the skin are known in the art. Exemplary lancing devices are shown, for example, in U.S. Pat. No. Re 35,803, issued to Lange, et al. on May 19, 1998; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Expressing

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of bodily fluid from an incision is the Amira AtLast blood glucose system.

Sampling

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite and Therasense FreeStyle test strips.

Testing General

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties on constituents.

Testing Difficulties

Performing the above-discussed steps can be difficult for patients, especially for patients with limited hand dexterity, such as the elderly. In a typical procedure, the patient first creates an incision in the skin by lancing the skin with the lancet. Once a sufficient amount of fluid collects as a droplet on the skin, the patient has to position a test strip over the incision site such that the test strip contacts and absorbs a sufficient amount of the fluid for testing. Usually, these droplet of fluid are quite small, and patients, especially ones with poor hand motor control, may experience great difficulty in positioning the test strip so as to collect an adequate sample from the droplet. As should be appreciated, a patient can become quickly frustrated by this procedure and, consequently, they may perform the test less often or may even quit testing altogether.

Thus, needs remain for further contributions in this area of technology.

SUMMARY

One aspect of the present invention concerns a method of sampling a bodily fluid. The method includes providing a bodily fluid sampling device that includes a lancet and a flexible test strip biased in position over the tip of the lancet. An incision is formed in the skin with the lancet. The test strip is released in order to be positioned over the incision site.

Another aspect concerns a bodily fluid sampling device. The device includes a lancet to form an incision in skin. A flexible test strip has a sampling end with a first position over the incision and a second position away from the incision. A deflection mechanism is operable to deflect the sampling end of the test strip from the first position to the second position in order to allow the lancet to form the incision. The test strip is resilient in order to return to the first position after the incision is formed.

A further aspect concern a bodily fluid sampling device that includes a lancet for forming an incision in skin. The device includes a flexible test strip that is biased to be positioned over the incision in skin and means for deflecting the test strip from the incision site.

Still yet another aspect concerns a bodily fluid sampling device that includes an incision forming member for forming an incision into skin. The device further includes means for analyzing bodily fluid from the incision in the skin. A deflection mechanism is configured to deflect the means for testing from the incision in the skin to allow the incision forming member clear access to the incision site.

Further forms, objects, features, aspects, benefits, advantages, and embodiments of the present invention will become apparent from a detailed description and drawings provided herewith.

DESCRIPTION OF SELECTED EMBODIMENTS

Figure 1:
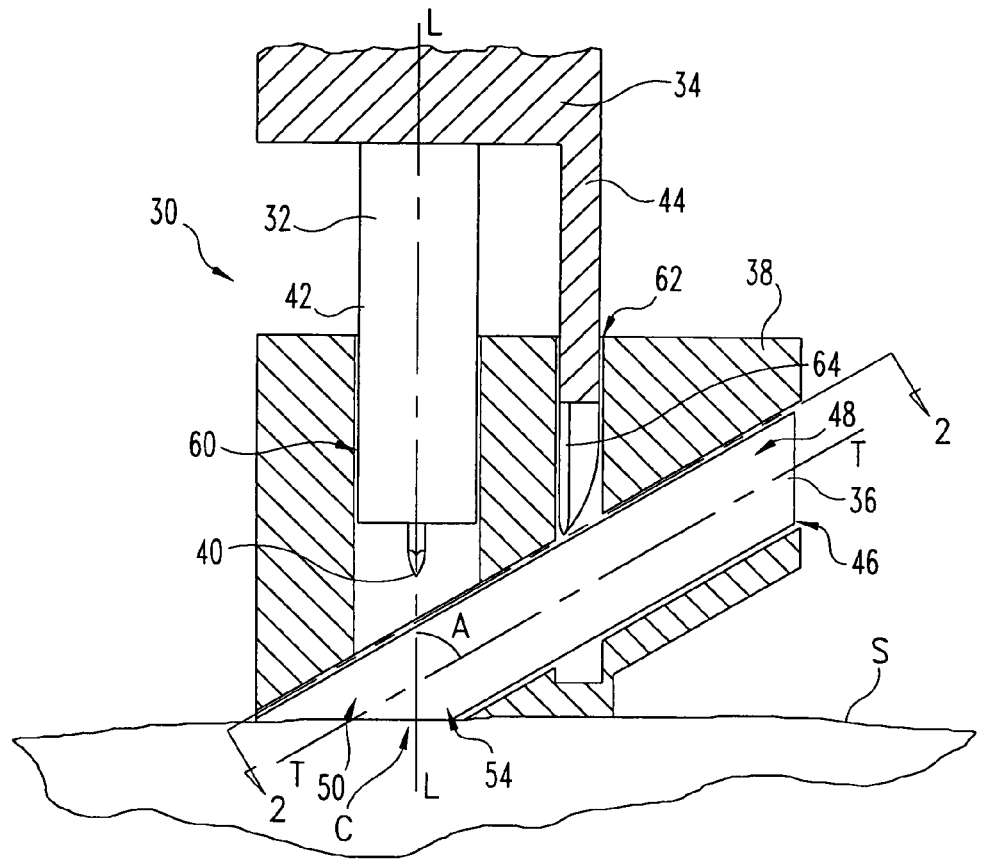
FIG. 1 is a side cross sectional view of a bodily fluid sampling device according to one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention generally concerns an integrated skin lancing device that reduces the number of steps involved in forming, collecting, and testing a bodily fluid sample from an incision. The device generally includes a lancet and a flexible test strip that has an end, which automatically positions itself over an incision site after lancing. In one embodiment, the lancet is coupled to a holder that has a cam arm, and the test strip is received inside a test strip holder. The test strip holder defines a lancet cavity in which the lancet is received and a cam arm cavity in which the cam arm of the lancet holder is received. The test strip extends between the lancet opening and the cam arm opening. The test strip holder further defines an expansion cavity in which the test strip is able to deflect. In one particular form, the test strip is oriented at an angle with respect to the lancet. During lancing, the test strip holder is positioned over the desired incision site. In this position, the test strip is aligned with the lancing tip of the lancet. During lancing, the cam arm is extended along with the lancet such that the cam arm bends the flexible test strip out of the way of the lancet so that the lancet is able to form the incision in the skin. After lancing the incision, the cam arm is retracted inside the cam cavity such that the test strip resiliently deflects back to its original position. At the original position, the test strip is positioned directly over the incision site, thereby the test strip is able to collect fluid from the incision site for analysis.

In another embodiment, one end of the test strip is attached to the lancet and the other end of the test strip is coupled to a release or catch mechanism that is pivotally mounted on the lancet. In one form, during cocking, the test strip is bent in a fashion similar to that of a bow, and the catch mechanism maintains the test strip in the cocked position. In the cocked position, the catch mechanism maintains the end of the test strip away from the tip of the lancet. The catch mechanism functions in a manner similar to that of a mouse trap. When the lancet lances the skin, the catch mechanism, through contact with the skin, releases the cocked test strip such that the end of the test strip is positioned over the incision site. Once the end of the test strip is positioned over the incision site, the fluid is then collected and deposited on the test strip for analysis. In another form, the catch mechanism cocks the test strip out of the way of the lancet upon contacting the skin during lancing and releases the test strip after lancing such that the end of the test strip is positioned over the incision site. In a further form, a trigger mechanism that fires the lancet is also used to deflect the test strip from the incision site.

An integrated bodily fluid sampling device 30 according to one embodiment of the present invention will now be described with reference to FIGS. 1–6. As shown in FIG. 1, the device 30 includes a lancet or incision forming member 32, a lancet holder 34 to which the lancet 32 is attached, a test strip or media 36 for analyzing bodily fluid and a test strip holder 38 to which the test strip 36 is attached. The lancet holder 34 is configured to deflect the test strip 36 out of the way of the lancet 32 during lancing. After lancing, the test strip 36 resiliently deflects back over the incision site in order to collect a fluid sample. For the sake of clarity and brevity, other components of device 30 that are well known, in the art, such as hammers, cocking mechanisms and the like that are not important to appreciate the present invention, will not be described below. For examples of such components, please refer to U.S. Pat. No. 5,964,718, issued to Duchon, et al., on Oct. 12, 1999, which is hereby incorporated by reference in its entirety. Sampling device 30 can be modified for incorporation into a number bodily fluid testing systems. For example, the sampling device 30 can be incorporated into a SOFTCLIX® brand lancing device (Boehringer Mannheim GmbH Corporation, Federal Republic of Germany).

Referring to FIG. 1, the lancet 32 has a lancet tip 40 configured to form an incision in skin S. The lancet tip 40 extends from a lancet body 42, which is attached to the lancet holder 34. In the illustrated embodiment, the lancet 32 has a generally cylindrical shape, but it should be appreciated that the lancet 32 can be shaped differently. For instance, the lancet 32 can be in the form of a flat lancet. In the illustrated embodiment, the lancet holder 34 has a cam or pusher arm 44 extending therefrom. As depicted in FIG. 1, the cam arm 44 extends in a generally parallel relationship with respect to the lancet 32. During lancing, the cam arm 44 is used to deflect the test strip 36 away from the lancet 32.

Figure 2:
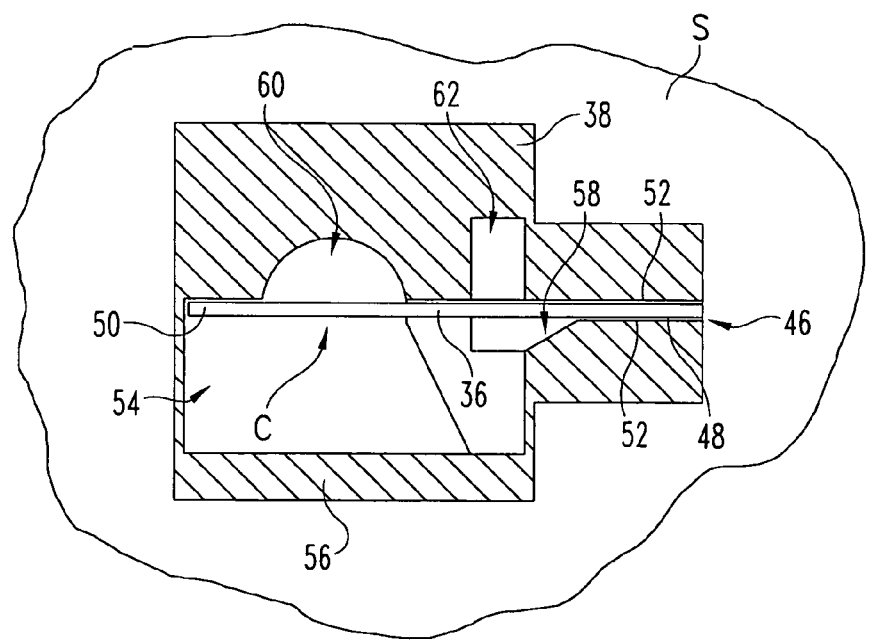
FIG. 2 is a cross sectional view of the FIG. 1 device taken along line 2—2 in FIG. 1.

The test strip 36 in the illustrated is operable to test analyte levels in a bodily fluid sample. The test strip 36 can analyze fluid through such means as optical (e.g., reflectance, absorption, fluorescence, RAMAN, etc.), electrochemical, and/or magnetic analysis, to name a few. In one embodiment, the test strip analyzes fluid optically through a chemical reagent. The test strip 36 is made from or contains material that makes the test strip 36 resilient. In one form, the test strip 36 includes a resilient backing strip made of a resilient material, such as plastic, and in another form, the test strip 36 is made from the resilient material. The test strip 36 in other embodiments can further include a wicking material that is used to draw bodily fluid onto the test strip 36. As shown, the test strip 36 is received in a test strip cavity 46 that is defined in the test strip holder 38. With reference to FIG. 1, the test strip 36 has a first end portion 48 and an opposite second end portion 50. The first end portion 48 of the test strip 36 in one embodiment is frictionally secured between walls 52 of the test strip cavity 46. It should be appreciated, however, that the test strip 36 can be secured in other manners. By way of nonlimiting examples, the test strip 36 can be secured through an adhesive and/or a clamp mechanism, to name a few. As shown in FIG. 2, the second end portion 50 of the test strip 36 is positioned inside a deflection cavity 54 that is defined in the test strip holder 38. In the illustrated embodiment, the deflection cavity 54 is enclosed by walls 56 of the test strip holder 38. It should be appreciated, however, that the deflection cavity 54 in other embodiments can be open to the outside environment. The deflection cavity 54 allows the second end portion 50 of the test strip 36 to deflect away from the lancet 32 during lancing. Between deflection cavity 54 and the test strip cavity 46, the test strip holder 38 has an angled deflection opening 58 that allows the test strip 36 to deflect away from the lancet 32.

Referring again to FIG. 1, the test strip holder 38 in the illustrated embodiment further defines a lancet cavity 60 in which the lancet 32 is slidably received and a cam arm cavity 62 in which the cam arm 44 of the lancet holder 34 is slidably received. Both the lancet cavity 60 and the cam arm cavity 62 intersect the test strip cavity 46 and the deflection cavity 54. The lancet 32 extends along a longitudinal axis L of the device 30, and the cam arm 44 extends in a parallel relationship with the longitudinal axis L. Inside the test strip cavity 46, the test strip 36 extends along a test strip axis T. As depicted in FIG. 1, the longitudinal axis L and the test strip axis T intersect one another at an acute angle A. By having the test strip 36 oriented at an acute angle A relative to the lancet 32 and the cam arm 44, the cam arm 44 is able to engage the test strip 36 before the lancet 32 contacts the test strip 36. This allows the cam arm 44 to be shorter than the lancet so that the cam arm 44 does not press against and deform the skin during lancing. In the illustrated embodiment, the cam arm 44 further incorporates an angled surface portion 64 that is engageable with the test strip 36 so as to aid in deflecting the test strip 36 during lancing.

Figure 3:
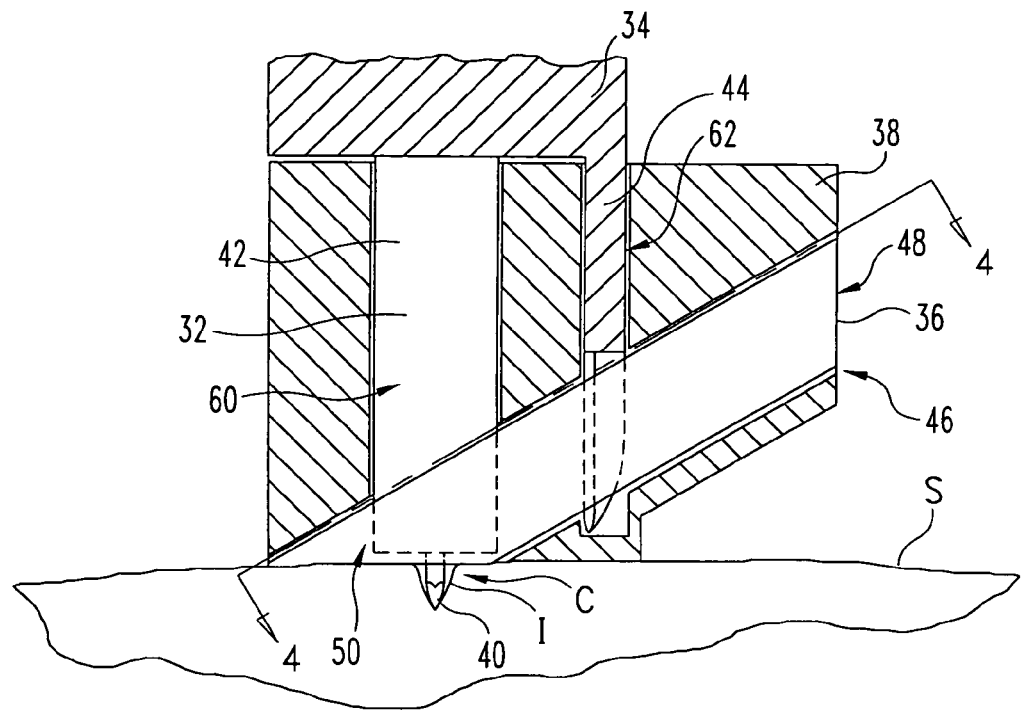
FIG. 3 is a side cross sectional view of the FIG. 1 device during lancing the skin.
Figure 4:
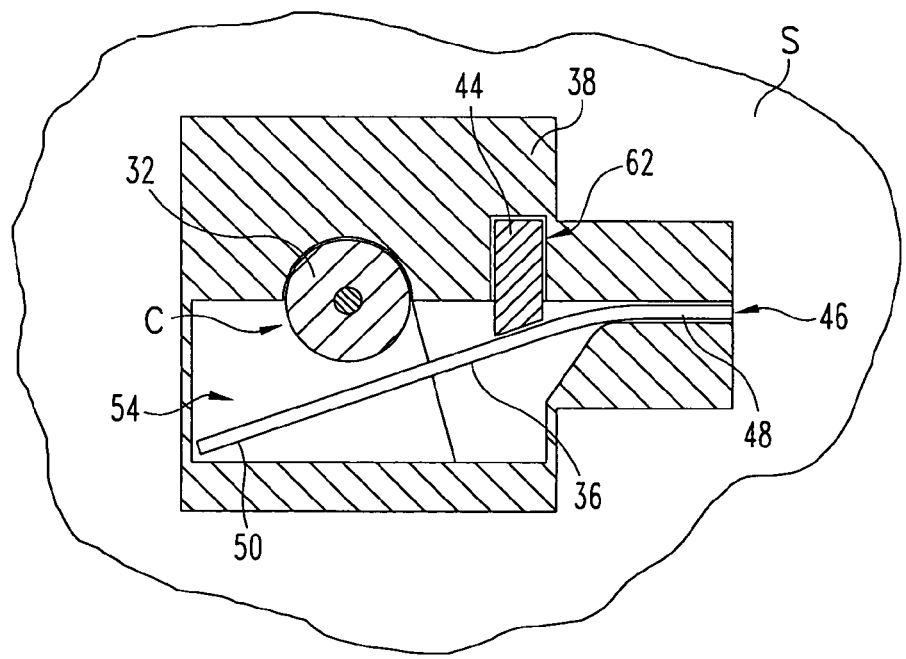
FIG. 4 is a cross sectional view taken along line 4—4 in FIG. 3.
Figure 5:
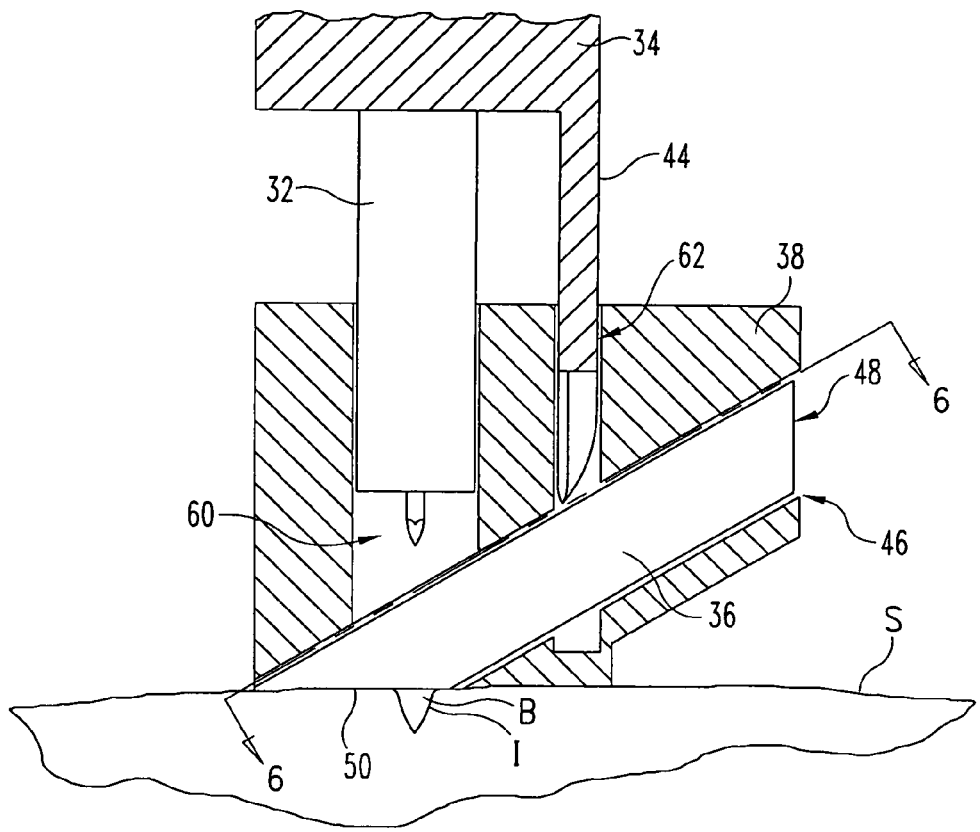
FIG. 5 is a side cross sectional view of the FIG. 1 device after lancing.
Figure 6:
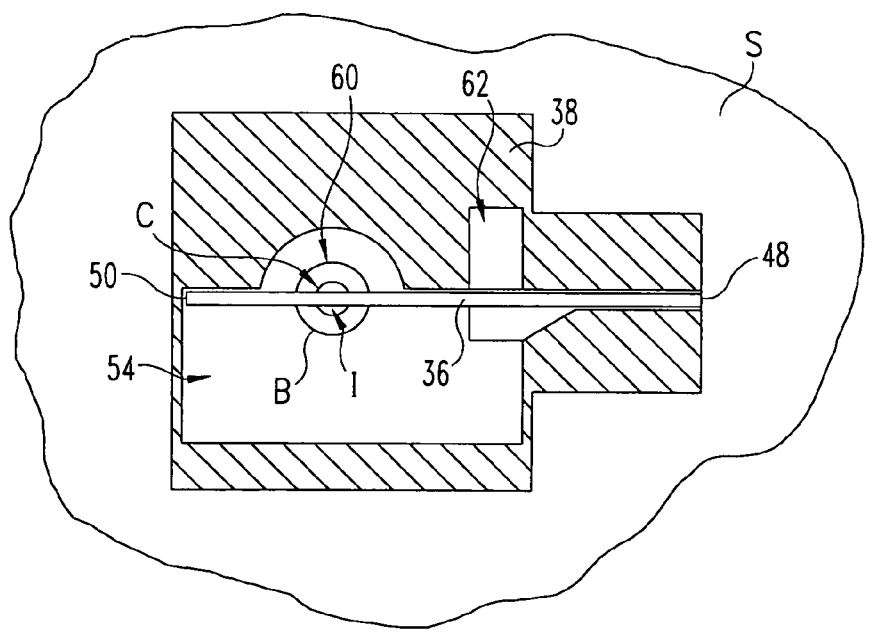
FIG. 6 is a cross sectional view of the FIG. 1 device taken along line 6—6 in FIG. 5.

Initially, before lancing, the second end portion 50 of the test strip 36 is positioned directly over incision site C. As should be appreciated, if the test strip 36 were not moved during lancing, the test strip 36 would obstruct the lancet 32 and thereby interfere with lancing of the skin S. The lancet 32 can be actuated or driven towards the skin S using actuation mechanisms as generally know by those skilled in the art. Referring to FIGS. 3 and 4, as the lancet holder 32 is actuated, the lancet 32 as well as the cam arm 44 are driven towards the skin S. Before the tip 40 of the lancet 32 can contact the test strip 36, the cam arm 44 engages the test strip 36, thereby deflecting the second end portion 50 of the test strip 36 away from the lancet 32 as well as the incision site C. This allows the lancet 32 to have an unobstructed path to the skin S such that the lancet tip 40 is able to form incision I. After the incision I is formed in the skin S, the lancet 32 is retracted from the skin S, as is shown in FIGS. 5 and 6. The lancet 32 can be retracted by retraction mechanisms of the type as generally known by those skilled in the art. For instance, the retraction mechanism can include a spring. As the lancet holder 34 retracts, the cam arm 44 disengages the test strip 36, and due to the resilient nature of the test strip 36, the test strip 36 returns to its original position over the incision I. By resiliently deflecting back over the incision I, the test strip 36 is able to collect bodily fluid B from the incision I. As should be appreciated, this simplifies the testing process because the test strip 36 is automatically positioned over the incision I. After a sufficient amount of bodily fluid B has been collected, the fluid B can be analyzed via the test strip 36.

It is contemplated that in a further embodiment the lancet 32 can be configured to act as the cam arm 44 and deflect the test strip 36 during lancing. In another embodiment, a capillary tube, or some other fluid collection means, can be incorporated into or replace the test strip 36. During lancing, the capillary tube is deflected by the cam arm 44 and resiliently returns to the position over the incision I such that the bodily fluid B can be collected in the capillary tube. The bodily fluid B in the capillary tube can be transported via capillary action to a test strip for analysis.

Figure 7:
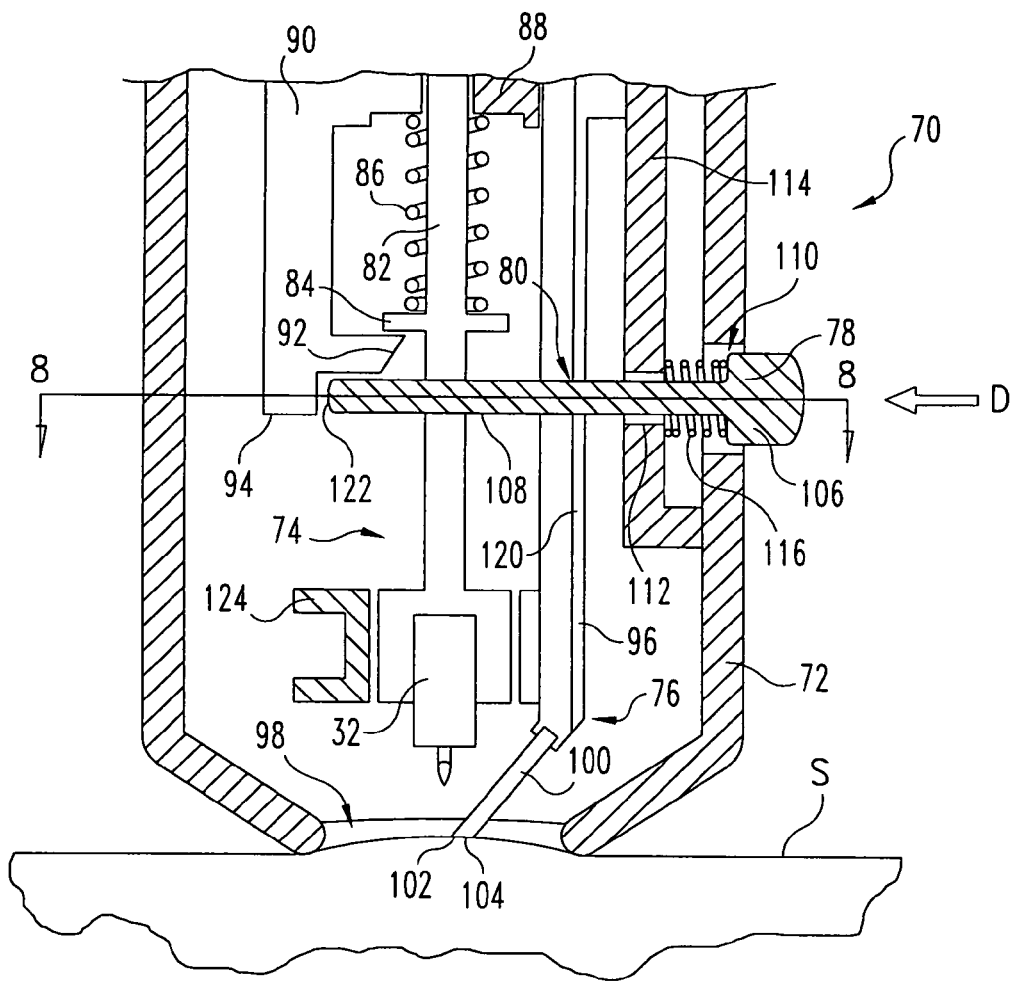
FIG. 7 is a side cross sectional view of a bodily fluid sampling device according to another embodiment of the present invention.
Figure 8:
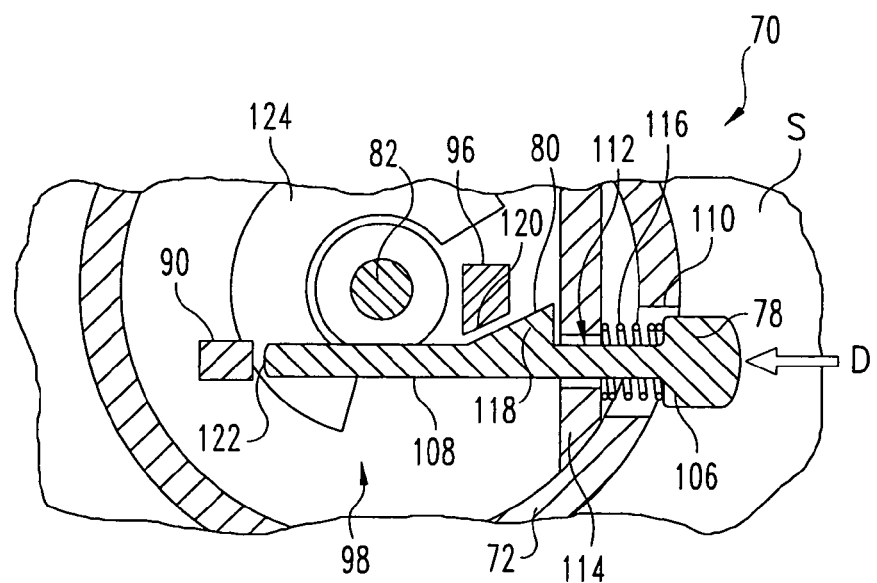
FIG. 8 is a cross sectional view of the FIG. 7 device taken along line 8—8 in FIG. 7.

A body fluid sampling device 70 according to another embodiment of the present invention is illustrated in FIGS. 7 and 8. As shown, the sampling device 70 includes a housing 72 that encloses a lancing mechanism 74 for forming an incision in the skin S and a sampling mechanism 76 for collecting a body fluid sample from the incision. The sampling device 70 further includes a trigger 78 for firing the lancing mechanism 74. As will be described in greater detail below, the trigger 78 has a deflection mechanism 80 that deflects the sampling mechanism 76 away from the lancing mechanism 74 during lancing.

Referring to FIG. 7, the lancing mechanism 74 has a firing arm 82 slidably coupled to the housing 72, and a lancet 32 for lancing the skin S is coupled to one end of the firing arm 82. The firing arm 82 has a cocking flange 84 for cocking the lancing mechanism 74. When the lancing mechanism 74 is cocked, a firing spring 86 is compressed between the cocking flange 84 and a spring retainer 88 in the housing 72. The lancing mechanism 74 is retained in the cocked position through a cocking arm 90 that is coupled to the housing 72. As shown, the cocking arm 90 has a tab 92 that engages the cocking flange 84 and a trigger engagement portion 94 that engages the trigger 78. In the illustrated embodiment, the cocking arm 90 is made of a resilient material, such as a resilient plastic. However, it is contemplated that the cocking arm 90 can be made resilient in other manners, such as by incorporating a spring, for example.

As briefly mentioned above, the sampling mechanism 76 is configured to collect a fluid sample. In the embodiment depicted in FIG. 7, the sampling mechanism 76 includes a deflection arm 96 that is coupled to the housing 72. The deflection arm 96 in the illustrated embodiment is made of a resilient material, such as a resilient plastic material, but it should be understood that the deflection arm 96 can be made resilient in other manners, such as through a spring. At one end near sampling opening 98 in the housing 72, the deflection arm 96 has a fluid collection element 100 that is configured to collect the fluid sample. In the illustrated embodiment, the fluid collection element 100 includes a test strip. Nevertheless, it should be understood that the fluid collection element 100 can include other types of structures for collecting fluid, such as a capillary tube or a tube capable of drawing fluid via a vacuum, to name a few. With the deflection arm 96 being resilient, the fluid collection element 100 does not necessarily have to be resilient. For example, in one embodiment, the fluid collection element 100 includes a relatively rigid test strip, but in other embodiments, it is contemplated that the fluid collection element 100 can be resilient. Referring to FIG. 7, the fluid collection element 100 extends at an oblique angle relative to the deflection arm 96 so that sampling end portion 102 of the fluid collection element 100 extends directly below the lancet 32. By positioning the fluid collection element 100 in such a manner, the fluid collection element 100 is able to be positioned directly over the incision, once formed. At the sampling end portion 102, the fluid collection element 100 has a sampling edge 104 that is beveled to match the contour of the skin S.

With reference to FIG. 8, the trigger 78 has a button portion or head 106 and an actuation arm or cam arm 108 that extends from the button head 106. As shown, the button head 106 is slidably disposed in a button opening 110 in the housing 72, and the actuation arm 108 is slidably disposed in a trigger opening 112 formed in a trigger retainer 114 in the housing 72. A trigger spring 116 is positioned between the trigger retainer 114 and the button head 106 in order to bias the trigger 78 into a normally cocked position. As mentioned above, the trigger 78 includes deflection mechanism 80 that biases the sampling mechanism 76 away from the lancet 32 during lancing. In the illustrated embodiment, the deflection mechanism 80 includes a deflection tab or cam tab 118 that is beveled to engage and deflect the deflection arm 96. It should be noted that the deflection tab 118 also acts as a stop that resists the pulling force of the trigger spring 116. The deflection arm 96 has a trigger engagement surface 120 that is beveled so as to engage the deflection tab 118. When the button head 106 is depressed in direction D, the deflection tab 118 on the trigger 78 engages the trigger engagement surface 120 on the deflection arm 96 such that the deflection arm 96 is bent, thereby moving the fluid collection element 100 away from the travel path of the lancet 32. Opposite the button head 106, the actuation arm 108 has an actuation end portion 122 that is configured to engage and bend the cocking arm 90 when the button head 106 is depressed. Once sufficiently bent, the cocking arm 90 disengages from the cocking flange 84 of the firing arm 82, thereby firing the lancing mechanism 74. In the illustrated embodiment, the actuation end portion 122 is sized in a manner so that the fluid collection element 100 is moved away from the incision site prior to the firing of the lancing mechanism 74.

Before using the sampling device 70, the lancing mechanism 74 is cocked by compressing the firing spring 86 and engaging the cocking flange 84 with the cocking arm 90. In one form, the lancing mechanism 74 is manually cocked by the user during replacement of the lancet 32. It, however, should be appreciated that the lancing mechanism 74 can be cocked in other manners. For instance, the lancing mechanism 74 in other embodiments can be cocked automatically with a motor. Once cocked, the user places the sampling opening 98 of the sampling device 70 against the skin S. In another form, the sampling device 70 can be placed against the skin S prior to cocking. To fire the lancet 32, the button head 106 of the trigger 78 is pressed in direction D. As the button head 106 is pressed, the deflection tab 118 bends the deflection arm 96 so that the fluid collection element 100 is clear of the incision site. When the trigger 78 is further pressed, the actuation end portion 122 of the trigger 78 engages and bends the cocking arm 90. Once sufficiently bent, the cocking arm 90 releases from the cocking flange 84 on the firing arm 82. The potential energy stored in the compressed firing spring 86 is released to fire the lancet 32 into the skin S so as to form an incision. In the illustrated embodiment, the housing 72 has one or more guide members 124 that direct the lancet 32 during lancing. After forming the incision, the lancet 32 is retracted from the skin S. In one form, the firing spring 86 is used to retract the lancet 32, but it is contemplated that the lancet 32 can be retracted in other manners. Upon lancing the skin S, the user releases the trigger 78, and the trigger spring 116 causes the button head 106 of the trigger 78 to return to its initial position. As the trigger 78 returns to its initial position, the deflection tab 118 of the trigger 78 disengages from the deflection arm 96, thereby allowing the fluid collection element 100 to return to its initial, undeflected position over the incision site. The fluid collection element 100 is then able to collect fluid from the incision for analysis, and in the case where the fluid collection element 100 is a test strip or incorporates some other means for analysis, the collected fluid can then be analyzed. If so desired, the trigger 78 can be repeatedly pressed and released so as to repeatedly wipe the fluid collection element 100 across the incision site to collect additional fluid around the incision site. As should be appreciated, the sampling device 70 illustrated in FIGS. 7 and 8 improves the firing speed of the lancet 32. With only the trigger mechanism 78 deflecting the fluid collection element 100, more of the energy stored in the lancing mechanism 74 can be used to lance the skin S, rather than being wasted in deflecting the fluid collection element 100.

While the invention has been illustrated and described in detail in the drawings and foregoing description, the same is to be considered as illustrative and not restrictive in character. It should be understood that only the preferred embodiment has been shown and described and that all changes, equivalents, and modifications that come within the spirit of the inventions defined by following claims are desired to be protected. All publications, patents, and patent application cited in this specification are herein incorporated by reference as if each individual publication, patent, or patent application were specifically and individually indicated to be incorporated by reference and set forth in its entirety herein.

What is claimed is:

1. A body fluid sampling device, comprising:
   a lancet configured to form an incision in skin;
   a sampling mechanism having a sampling end disposed proximal to the lancet that is moveable between a first position over the incision and a second position where the sample end is located farther away from the incision than at the first position;
   a deflection mechanism engageable with the sampling mechanism to deflect the sampling end of the sampling mechanism from the first position to the second position in order to allow the lancet to form the incision; and
   wherein at least a portion of the sampling mechanism is resilient in order to return to the first position after the incision is formed.

2. The device of claim 1, wherein the sampling mechanism includes a fluid collection element.

3. The device of claim 2, wherein the fluid collection element includes a test strip.

4. The device of claim 2, wherein the fluid collection element is resilient.

5. The device of claim 2, wherein the sampling mechanism includes a deflection arm that is coupled to the fluid collection element.

6. The device of claim 5, wherein the deflection mechanism includes a trigger configured to fire the lancet.

7. The device of claim 1, wherein the deflection mechanism includes a trigger configured to fire the lancet.

8. The device of claim 1, wherein the deflection mechanism includes a cam arm coupled to the lancet to move in unison with the lancet.

9. The device of claim 8, wherein the cam arm has an angled surface that is engageable with the sampling mechanism to deflect the sampling mechanism.

10. The device of claim 8, wherein the sampling mechanism includes a fluid collection element.

11. The device of claim 10, further comprising a holder defining a cam arm cavity in which the cam arm is slidably received, the holder defining a fluid collection element cavity in which the fluid collection element is received, wherein the cam arm cavity intersects the fluid collection element cavity.

12. The device of claim 11, wherein:
    the holder defines a lancet cavity in which the lancet is slidably received; and
    the holder defines a deflection cavity in which the fluid collection element is able to deflect.

13. The device of claim 10, wherein the fluid collection element is angled at an acute angle relative to the lancet to allow the cam arm to deflect the fluid collection element before the lancet is able to strike the fluid collection element.

14. The device of claim 1, wherein the sampling end portion of the sampling mechanism is angled at an acute angle relative to the lancet.

15. A body fluid sampling device, comprising:
    a lancet configured to cut an incision in skin;
    a test strip extending over a position where the lancet cuts the incision;
    a cam arm coupled to the lancet to move in unison with the lancet as the lancet travels to cut the incision, the cam arm being positioned to bend the test strip from the position where the lancet cuts the incision; and
    the test strip being configured to spring back over the incision to collect body fluid once the lancet retracts from the incision.

16. The device of claim 15, wherein the test strip is angled at an acute angle relative to the lancet to allow the cam arm to bend the test strip before the lancet is able to strike the test strip.

* * * * *